US011865296B2

(12) United States Patent
Boukidjian et al.

(10) Patent No.: US 11,865,296 B2
(45) Date of Patent: Jan. 9, 2024

(54) CATHETER SYSTEM FOR DRAINING A BODILY FLUID FROM A FLUID SOURCE IN A BODY

(71) Applicant: DIGNITY HEALTH, San Francisco, CA (US)

(72) Inventors: Roy Boukidjian, Winnetka, CA (US); Gregoire Boukidjian, Winnetka, CA (US)

(73) Assignee: DIGNITY HEALTH, San Francisco, CA (US)

( * ) Notice: Subject to any disclaimer, the term of this patent is extended or adjusted under 35 U.S.C. 154(b) by 341 days.

(21) Appl. No.: 16/337,378

(22) PCT Filed: Aug. 3, 2017

(86) PCT No.: PCT/US2017/045239
§ 371 (c)(1),
(2) Date: Mar. 27, 2019

(87) PCT Pub. No.: WO2018/063499
PCT Pub. Date: Apr. 5, 2018

(65) Prior Publication Data
US 2020/0030595 A1    Jan. 30, 2020

Related U.S. Application Data

(60) Provisional application No. 62/401,777, filed on Sep. 29, 2016.

(51) Int. Cl.
*A61M 39/24* (2006.01)
*A61F 5/44* (2006.01)
*A61M 25/00* (2006.01)

(52) U.S. Cl.
CPC ............... *A61M 39/24* (2013.01); *A61F 5/44* (2013.01); *A61M 25/0017* (2013.01); *A61M 2039/248* (2013.01); *A61M 2202/0496* (2013.01)

(58) Field of Classification Search
CPC .... A61M 1/0035; A61M 39/223; A61M 1/00; A61M 39/22; A61M 5/168;
(Continued)

(56) References Cited

U.S. PATENT DOCUMENTS 3,943,929 A    3/1976  Patel
4,216,791 A *  8/1980  Browne ................ A61M 39/22
                                                            137/199
(Continued)

FOREIGN PATENT DOCUMENTS

GB    2472407        2/2011
GB    2472407 A  *  2/2011  ............ A61M 25/10

OTHER PUBLICATIONS

Association for Professionals in Infection Control and Epidemiology, Inc. APIC Implementation Guide—Guide to Preventing Catheter-Associated Urinary Tract Infections. Apr. 2014. In four parts due to file size.
(Continued)

*Primary Examiner* — Sarah Al Hashimi
*Assistant Examiner* — Nhu Q. Tran
(74) *Attorney, Agent, or Firm* — QUARLES & BRADY LLP

(57) ABSTRACT

A catheter system for draining a bodily fluid from a fluid source in a body of a subject. In one form, the catheter tube has a proximal end and a distal end. The catheter tube includes a drainage lumen that extends from a proximal end opening in the proximal end to a distal end opening in the distal end. The catheter system further includes a fluid (Continued)

sampling component in fluid communication with the distal end opening. In some embodiments, the catheter system includes a one-way check valve. In some embodiments, the catheter system includes a balloon positioned between one or more openings.

14 Claims, 12 Drawing Sheets

(58) Field of Classification Search
CPC ........ A61M 5/16877; A61M 2039/248; A61M 39/24; A61M 27/00; F16K 1/14
See application file for complete search history.

(56) References Cited

U.S. PATENT DOCUMENTS

| | | | |
|---|---|---|---|
| 4,705,502 | A | 11/1987 | Patel |
| 5,405,336 | A | 4/1995 | Austin et al. |
| 6,045,531 | A | 4/2000 | Davis |
| 6,364,868 | B1 | 4/2002 | Ikeguchi |
| 7,331,949 | B2 | 2/2008 | Marisi |
| 7,670,332 | B2 | 3/2010 | O'Keefe |
| 8,137,309 | B2 | 3/2012 | Nishtala |
| 8,177,765 | B2 | 5/2012 | House |
| 8,522,813 | B2 | 9/2013 | McElroy |
| 8,920,403 | B2 | 12/2014 | Doerr |
| 2005/0101941 | A1 | 5/2005 | Hakky |
| 2007/0203463 | A1 | 8/2007 | Salvadori |
| 2007/0270734 | A1 | 11/2007 | Crisp |
| 2008/0262477 | A1 | 10/2008 | Djaladat |
| 2008/0281284 | A1 | 11/2008 | Garfield |
| 2011/0238042 | A1* | 9/2011 | Davis ................ A61M 25/0017 604/544 |
| 2012/0232503 | A1 | 9/2012 | Macy, Jr. |
| 2013/0079756 | A1 | 3/2013 | House |
| 2013/0245496 | A1 | 9/2013 | Wells |
| 2014/0137949 | A1* | 5/2014 | Montague ................ E03B 9/16 137/300 |
| 2015/0094695 | A1 | 4/2015 | Daniel |
| 2015/0141965 | A1 | 5/2015 | Bonham |
| 2015/0359996 | A1 | 12/2015 | Arora |
| 2016/0310711 | A1* | 10/2016 | Luxon ............... A61M 25/0017 |
| 2017/0014617 | A1* | 1/2017 | Huici ................ A61M 39/0606 |

OTHER PUBLICATIONS

CDC.gov. FAQ's about "Catheter-Associated Urinary Tract Infection". Accessed online at https://www.cdc.gov/hai/pdfs/uti/CA-UTI_tagged.pdf. Version retrieved on Jul. 28, 2016 at https://web.archive.org/web/20160728000547/https://www.cdc.gov/hai/pdfs/uti/CA-UTI_tagged.pdf.

European Patent Office, Extended European Search Report and Written Opinion for application 17856968.7, dated Apr. 30, 2020.

International Searching Authority, International Search Report and Written Opinion for application PCT/US2017/045239, dated Oct. 18, 2017.

Maki, D. G., et al. "Engineering out the risk for infection with urinary catheters." Emerging infectious diseases 7.2 (2001): 342.

medlineplus.gov. Catheter-Related UTI. Accessed online at https://medlineplus.gov/ency/article/000483.htm. Version updated Jul. 7, 2016.

National Clinical Guideline Centre. "Infection: prevention and control of healthcare-associated infections in primary and community care: partial update of NICE Clinical Guideline 2." London: Royal College of Physicians, 2012. In two parts due to file size.

Wenzler-Rottele, S., et al. "Comparison in a laboratory model between the performance of a urinary closed system bag with double non-return valve and that of a single valve system." Infection 34.4 (2006): 214-218.

* cited by examiner

CATHETER SYSTEM FOR DRAINING A BODILY FLUID FROM A FLUID SOURCE IN A BODY

CROSS REFERENCE TO RELATED APPLICATIONS

This application is a U.S. National Stage of PCT Application No. PCT/US2017/045239 filed on Aug. 3, 2017 which claims the benefit of U.S. Provisional Patent Application No. 62/401,777, filed on Sep. 29, 2016, the entire contents of which are incorporated herein by reference.

STATEMENT REGARDING FEDERALLY SPONSORED RESEARCH

Not Applicable.

BACKGROUND OF THE INVENTION

1. Field of the Invention

This invention relates to a catheter system for draining a bodily fluid from a fluid source in a body. More particularly, the invention relates to a catheter system for draining urine from the bladder.

2. Description of the Related Art

An indwelling catheter is a catheter that is inserted into the bladder and allowed to remain in the bladder for a few hours to several weeks. A Foley catheter is a common type of indwelling urinary catheter. A Foley catheter generally includes a thin, flexible tube that can be inserted into the bladder to drain urine. It is held in place with a balloon at the end that lies inside the bladder. The balloon is inflated with a fluid to prevent the catheter from being removed from the bladder. The tube of a Foley catheter has two separate lumens running down its length. One lumen is open at both ends and allows urine to drain into the collection bag. The other lumen has a valve on an outside end and connects to the balloon at a tip to allow for inflation of the balloon with fluid.

It has been reported that urinary tract infections are one of the five most common types of healthcare-associated infections. A majority of healthcare-associated urinary tract infections are caused by instrumentation of the urinary tract. Catheter-associated urinary tract infection has been associated with increased morbidity, mortality, hospital cost, and length of stay. Bacteriuria also leads to unnecessary antimicrobial use, and urinary drainage systems can be reservoirs for multidrug-resistant bacteria and a source of transmission to other patients. A urinary catheter provides a portal of entry into the urinary tract. Bacteria may ascend into the tract via the external or internal surface of the catheter. In internal (intraluminal) bacterial ascension, microbes may ascend from the urine collection bag, through the catheter, into the bladder via reflux. Furthermore, biofilm formation can occur within the catheter, and damage to bladder mucosa facilitates biofilm on this surface. Reflux, or backflow, then carries bacteria and other components of the biofilm into the bladder. See, "Guide to Preventing Catheter-Associated Urinary Tract Infections", Association for Professionals in Infection Control and Epidemiology, Inc., 2014.

Conventional Foley urinary catheters have a urine extraction port located near the patient's genitalia. Hospital staff have to manipulate the catheter tube in order to have enough urine at the port for withdrawal. This increasingly causes risk of the urine to back-flow into the bladder causing infections. Prevention of urine backflow relies on ensuring the collection bag is below the bladder level at all times, which does not always occur (patient using a walker or being transferred from one bed to another, etc.). The nurse needs to ensure consistent practice manually. Improving bladder emptying is not currently resolved, and urine collection now relies on the nurse to manipulate tubing and clamping in order to collect specimen from the collection port.

As noted above, conventional Foley urinary catheters have a balloon which inflates within the bladder. The balloon rests directly on top of the urethra opening. This causes blockage. At this point, the urine must fill the bladder until it reaches an opening above the balloon at the tip of the lumen of the catheter. Once the urine level drops below opening, the remaining urine sits in the bladder until more urine is produced. This may be a cause of infections as the stagnant urine is a breeding ground for bacteria. The urine being produced at this point is mixing with the urine that has been sitting in the bladder. Due to a lack of directional flow during urine production, it cannot be guaranteed that the old urine will flow out as the new urine is produced.

Therefore, what is needed is an improved catheter system for draining urine from the bladder.

SUMMARY OF THE INVENTION

According to one embodiment, there is provided a catheter system for draining a bodily fluid from a fluid source in a body of a subject. The catheter system may comprise a catheter tube having a proximal end, a distal end, and an intermediate portion between the proximal end and the distal end. The catheter tube may include a drainage lumen that extends from a proximal end opening in the proximal end to a distal end opening in the distal end. The catheter system may further include a one way check valve that has an open position in which the bodily fluid can flow in a downstream direction from the proximal end toward the distal end and a closed position in which the bodily fluid cannot flow in an upstream direction from the distal end toward the proximal end. The check valve may be positioned in the drainage lumen at the intermediate portion of the catheter tube such that the check valve is outside the body of the subject when the proximal end opening is located in the fluid source in the body of the subject.

According to another embodiment, there is provided a catheter system for draining a bodily fluid from a fluid source in a body of a subject. The catheter system may comprise a catheter tube having a proximal end and a distal end. The catheter tube may include a drainage lumen that extends from a proximal end opening in the proximal end to a distal end opening in the distal end. The catheter system may further comprise a fluid sampling component in fluid communication with the distal end opening.

According to another embodiment, there is provided a catheter system for draining a bodily fluid from a fluid source in a body of a subject. The catheter system may comprise a catheter tube having a proximal end, a distal end, and an intermediate portion between the proximal end and the distal end. The catheter tube may include a drainage lumen that extends from a proximal end opening in the proximal end to a distal end opening in the distal end. The catheter system may further include a one way check valve that has an open position in which the bodily fluid can flow in a downstream direction from the proximal end toward the distal end and a closed position in which the bodily fluid cannot flow in an upstream direction from the distal end toward the proximal end. The check valve may be positioned in the drainage lumen at the intermediate portion of the catheter tube such that the check valve is outside, but may be substantially or immediately adjacent to the body of the subject when the proximal end opening is located in the fluid source in the body of the subject. The catheter system may further comprise a fluid sampling component in fluid communication with the distal end opening.

It is therefore an advantage of the invention to provide a catheter system for draining urine from the bladder wherein the catheter system prevents urine reflux or backflow from the catheter tubing back into the bladder (e.g., due to gravity).

It is another advantage of the invention to provide a catheter system for draining urine from the bladder wherein the catheter system includes a balloon and opening of the catheter tubing that improves emptying and eliminates any residual urine that is caused by the balloon.

It is another advantage of the invention to provide a catheter system for draining urine from the bladder wherein the catheter system improves urine collection by removing the need to kink the tubing and adjust tubing location in order to draw a urine sample from the collection port.

It is another advantage of the invention to provide a catheter system for draining urine from the bladder wherein the catheter system reduces both the potential for an infection and urine collection time.

It is another advantage of the invention to provide a catheter system for draining urine from the bladder wherein the catheter system automates the prevention of urine backflow versus the manual need to ensure proper placement of the drainage bag (e.g., below the bladder).

These and other features, aspects, and advantages of the present invention will become better understood upon consideration of the following detailed description, drawing and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
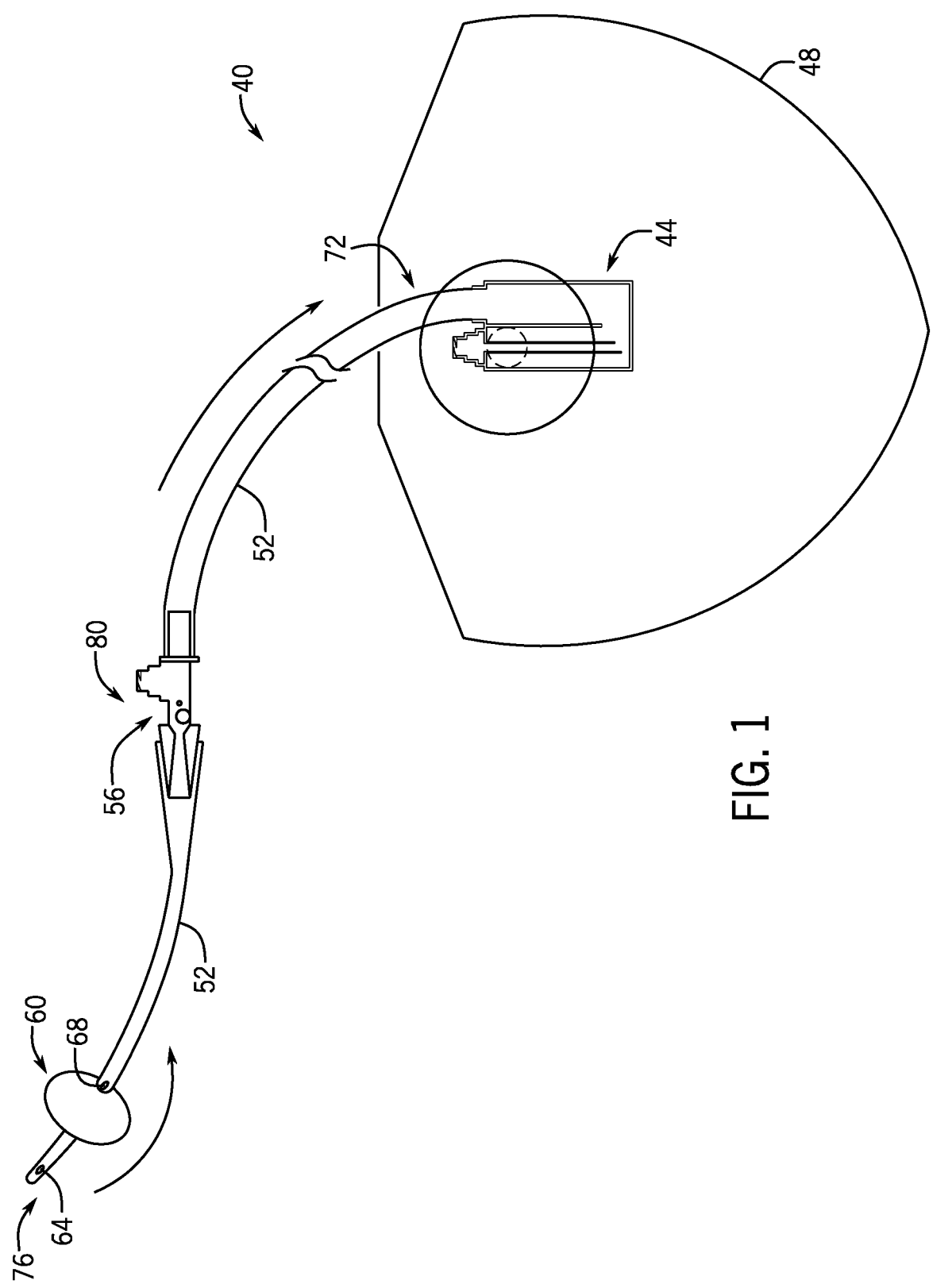
FIG. 1 is a side view of a catheter system for draining fluid from a fluid source according to one example embodiment of the present invention.
Figure 2:
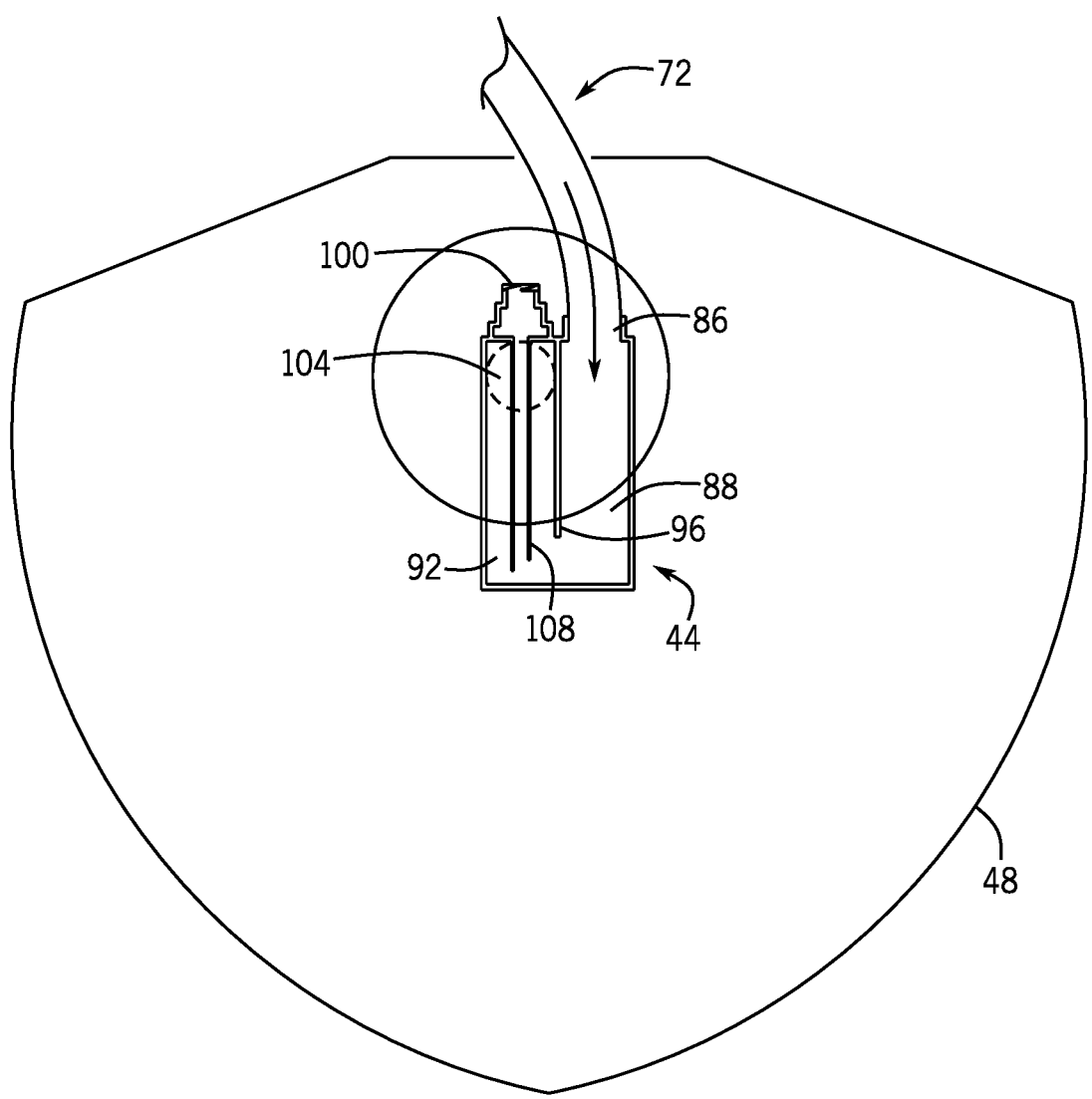
FIG. 2 is a detailed side view of a urine collection container and fluid sampling component of the catheter system of FIG. 1.
Figure 3:
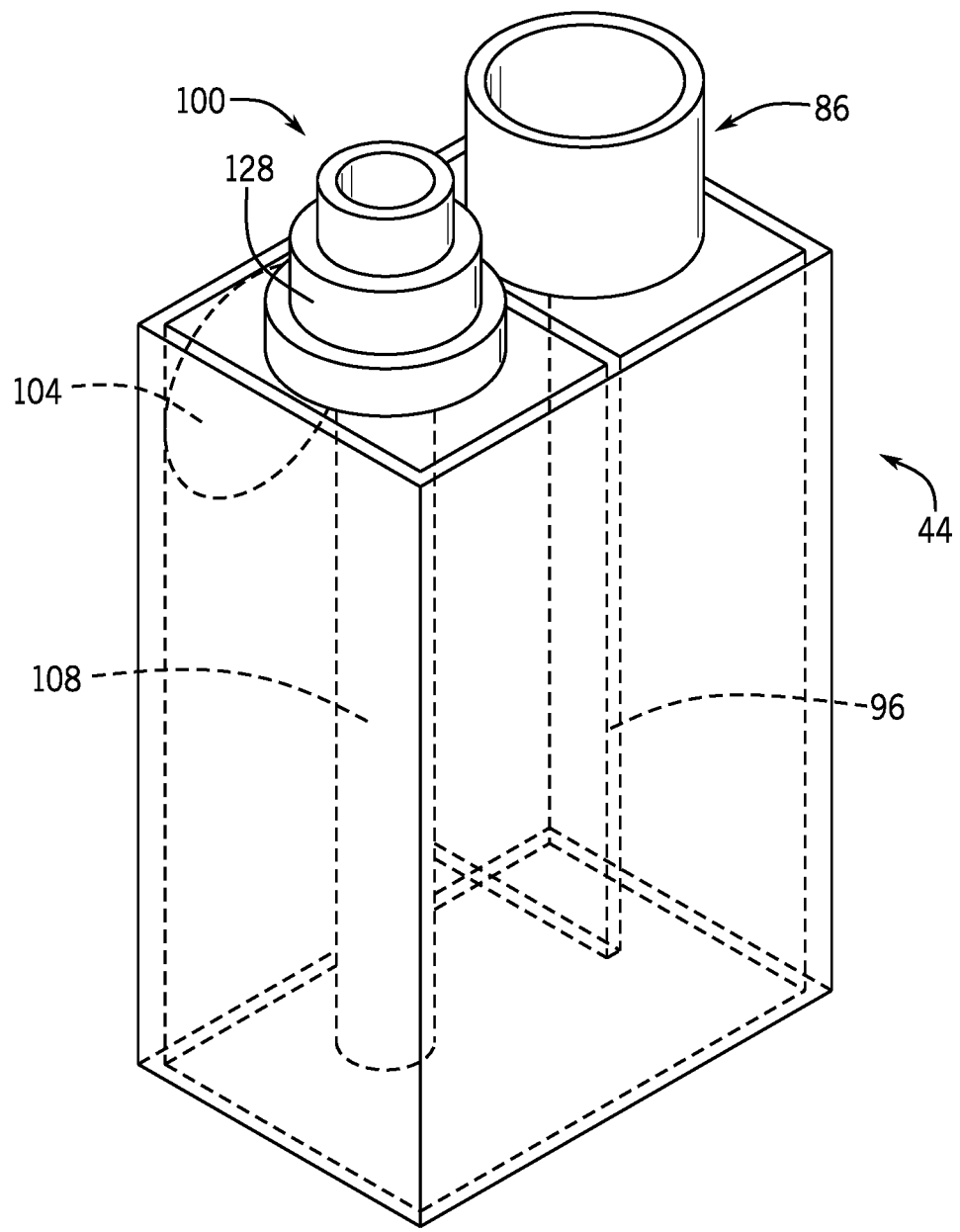
FIG. 3 is a perspective view of the fluid sampling component of the catheter system of FIG. 1.
Figure 4:
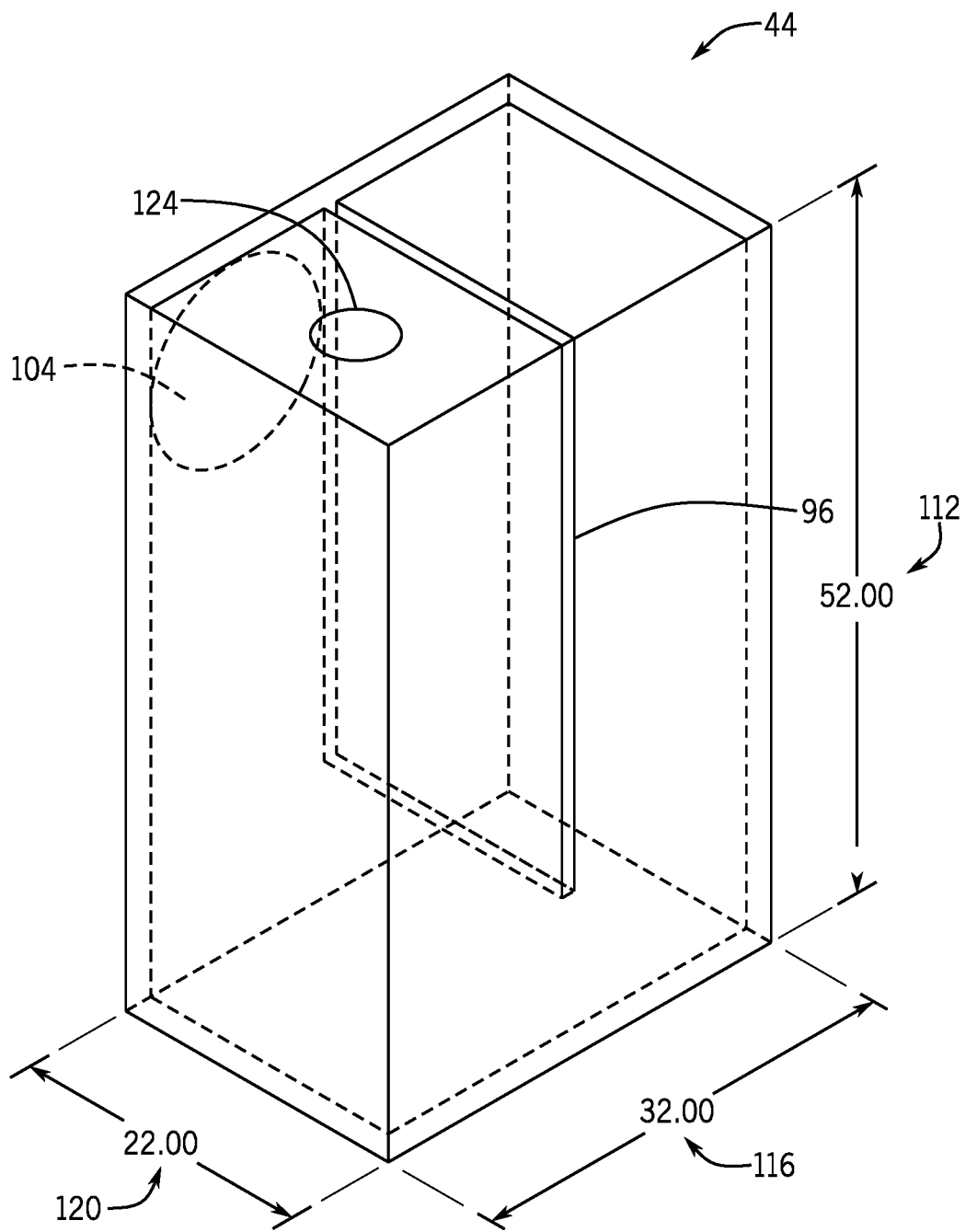
FIG. 4 is a perspective view of a container of the fluid sampling component of FIG. 3.
Figure 5:
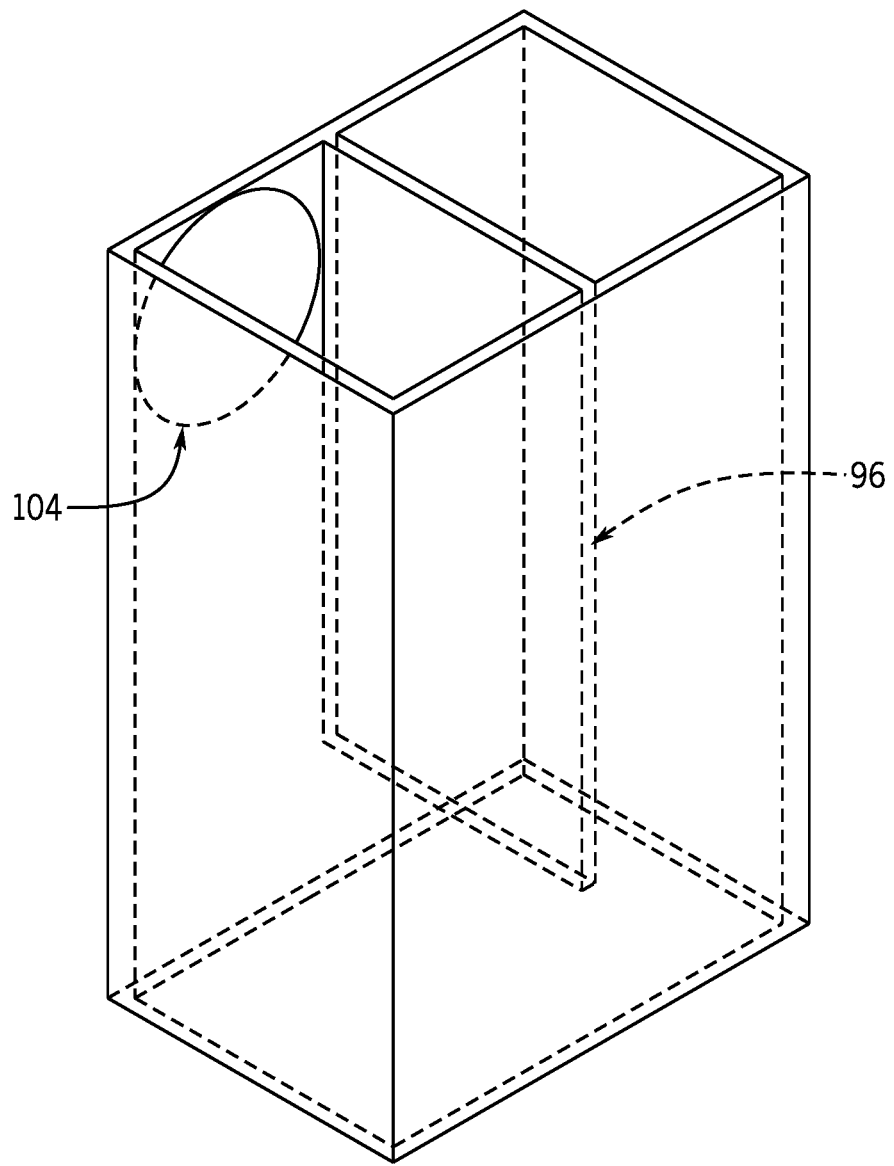
FIG. 5 is another perspective view of the container of the fluid sampling component of FIG. 3.
Figure 6:
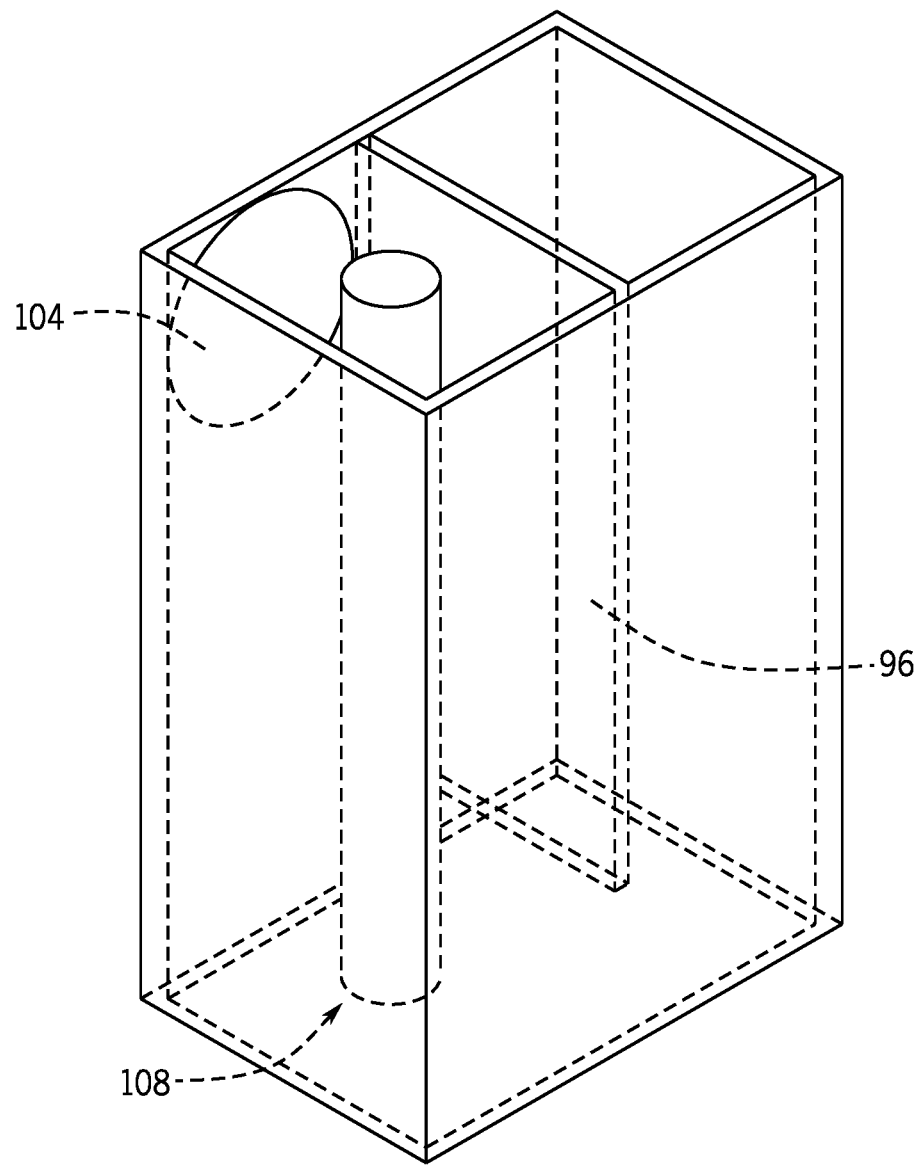
FIG. 6 is another perspective view of the container of the fluid sampling component of FIG. 3.
Figure 7:
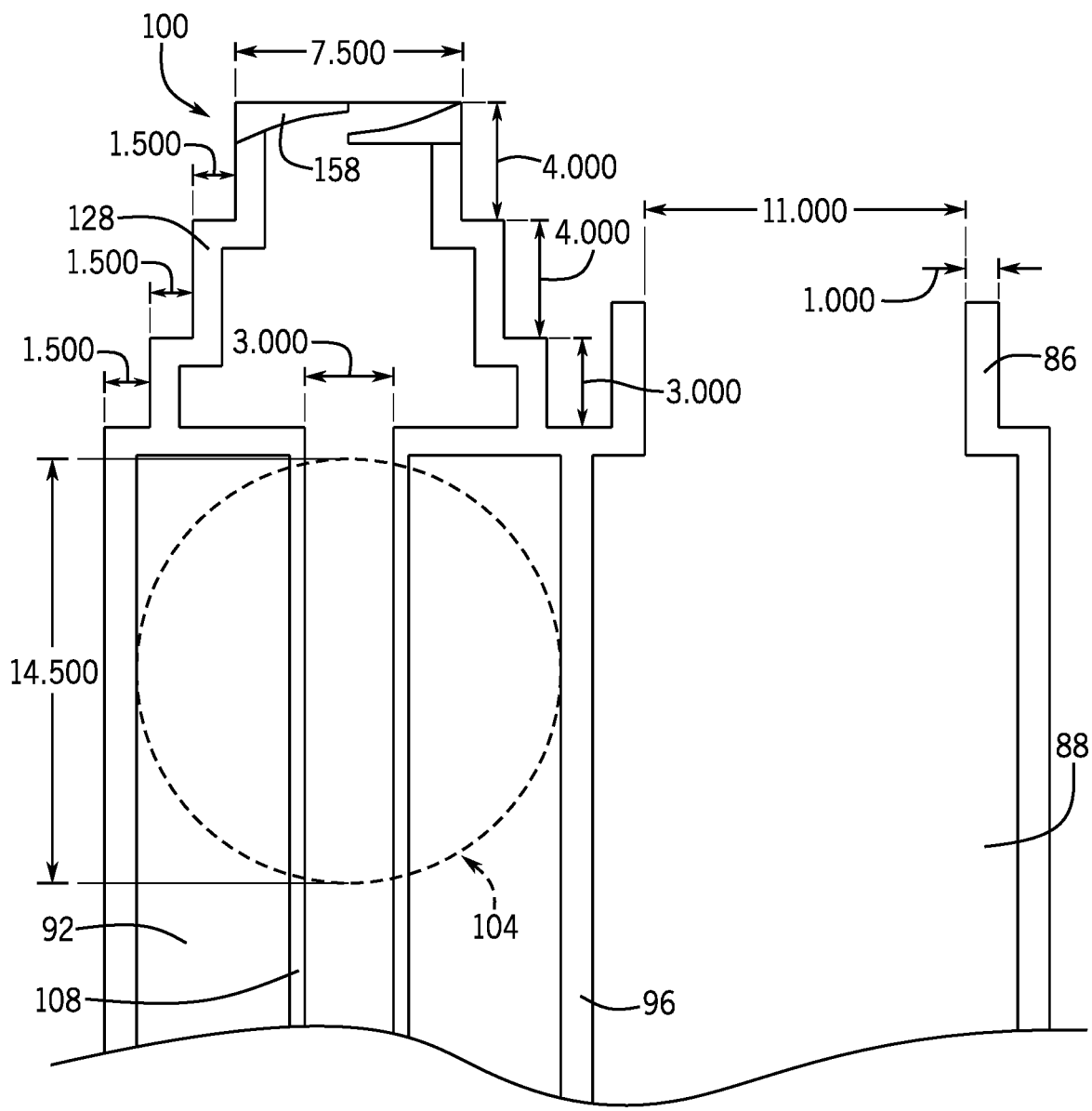
FIG. 7 is a detailed partial cross-sectional view of the fluid sampling component of FIG. 3.
Figure 8:
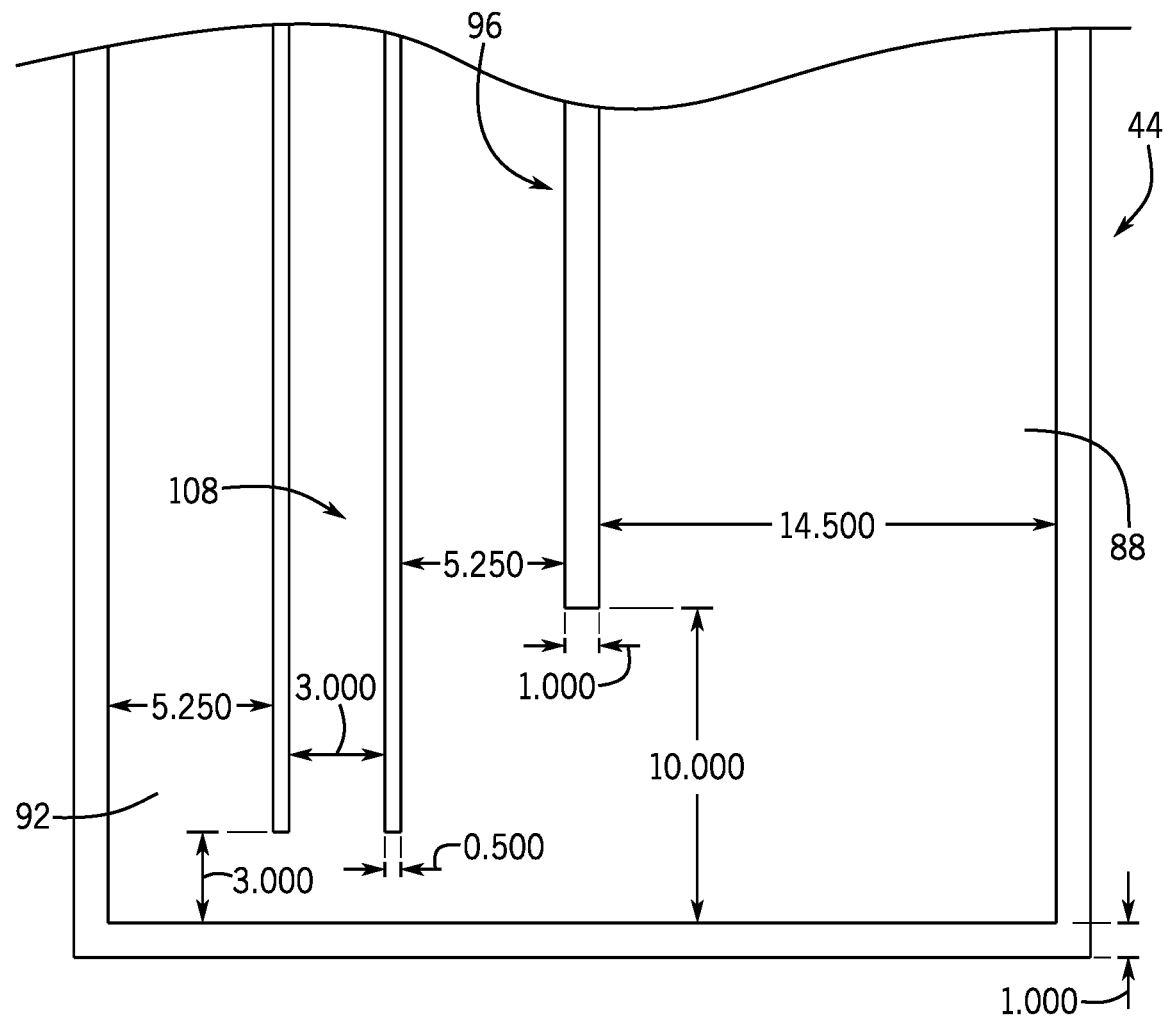
FIG. 8 is another detailed partial cross-sectional view of the fluid sampling component of FIG. 3.
Figure 9:
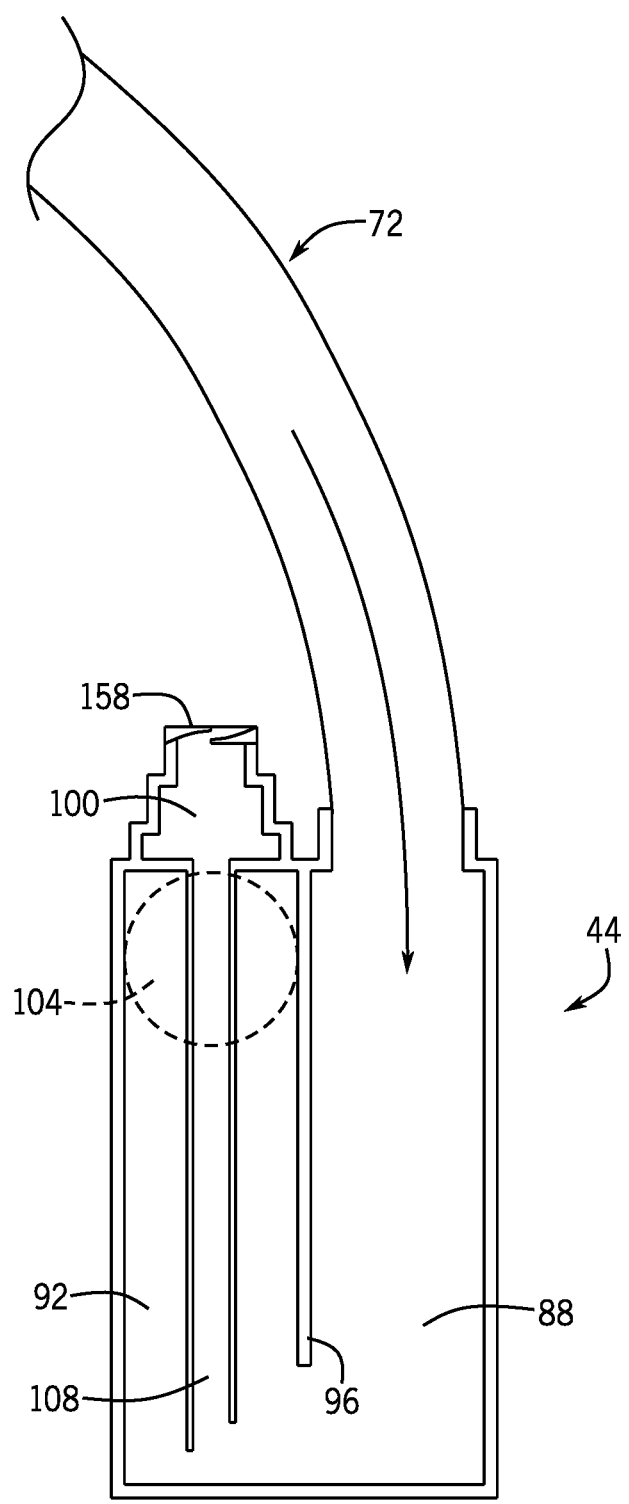
FIG. 9 is a detailed cross-sectional view of the fluid sampling component of FIG. 3.

Referring to FIG. 1, a catheter system 40 may include a fluid sampling component 44, a fluid collection container 48, a catheter tube 52, a one-way check valve 56, a balloon 60, an opening 64 in the catheter tube 52, and a second opening 68 in the catheter tube 52. The catheter tube 52 may have a distal end 72 and a proximal end 76, and an intermediate portion between the proximal end 76 and the distal end 72. The proximal end 76 may be configured to be placed in a subject while the distal end 72 may be configured to be outside of a subject. The catheter tube 52 includes at least one drainage lumen (not shown) that extends from the proximal end 76 to the distal end 72 of the catheter tube 52. The drainage lumen may provide fluid communication between the proximal end 76 and the distal end 72 of the catheter tube 52. The fluid sampling component 44 may be positioned at or near the distal end 72 of the catheter tube 52 and may be connected to the fluid collection container 48 (e.g., a fluid collection bag). The catheter tube 52 may extend away from the fluid sampling component 44 and the fluid collection container 48 and the one-way check valve 56 may be disposed within the drainage lumen of the catheter tube 52 at an intermediate location 80 (i.e., along the intermediate portion of the catheter tube 52 between the proximal end 76 and the distal end 72). In some aspects, the intermediate location 80 may be disposed substantially adjacent to the proximal end 76. As such, upon positioning of the proximal end 76 of the catheter tube 52 within a body, the intermediate location 80/the one-way check valve 56 may be positioned substantially or immediately adjacent to the body. In other embodiments, the intermediate location 80 may be disposed at any other position along a length of the catheter tube 52. Illustratively, the catheter tube 52 may further extend away from the one-way check valve 56 toward the proximal end 76. A balloon 60 may be positioned between the opening 64 and the second opening 68. The opening 64 may be proximal to the balloon 60 and the second opening 68 may be distal to the balloon 60. The opening 64 and the second opening 68 may provide fluid to enter the drainage lumen of the catheter tube 52. The catheter tube 52 may be of any appropriate length and may be selectively flexible. In some embodiments, the catheter tube 52 may be one continuous tube. In other embodiments, the catheter tube 52 may be two or more pieces that may be connected together, illustratively, at the one-way check valve 56.

Referring to FIGS. 2-9, the fluid sampling component 44 may be connected to the fluid collection container 48 and may further connect the distal end 72 of the catheter tube 52 to the fluid collection container 48. The fluid sampling component 44 may be a container or container-like component with walls 112, 116, 120 each having varying or similar lengths. The walls 112, 116, 120 may enclose an upstream portion 88 and a downstream portion 92 that are in fluid communication with each other and are partially separated by a wall 96. The upstream portion 88 may interface with the distal portion 72 of the catheter tube 52 via an inlet 86 to the fluid sampling component 44. The inlet 86 may be cylindrical in shape and may extend vertically from a top surface of the fluid sampling component 44. The wall 96 extends downwardly and bifurcates the fluid sampling component 44 thereby creating the upstream portion 88 and the downstream portion 92. A sampling port 100 is connected to the downstream portion 92 of the fluid sampling component 44 and is positioned above an inlet 104 to the fluid collection container 48. The inlet 104 to the fluid collection container 48 may be a circular opening positioned on a side wall near the top of the downstream portion 92. The sampling port 100 may outwardly extend from an outer surface of the fluid sampling component 44 and is connected to the downstream portion 92 via an extraction tube 108 that extends into the downstream portion 92. The extraction tube 108 may be cylindrical in shape and may have a hollow interior channel that may facilitate fluid communication between the sampling port 100 and the downstream portion 92. The outward extension of the sampling port 100 is supported by a sampling port support body 128 that has three cylindrical protrusions, the base cylindrical protrusion having the largest outer diameter and the top cylindrical protrusion having the smallest outer diameter. The sampling port 100 may be in fluid communication with the extraction tube 108 via an inlet 124 to the extraction tube 108. In some embodiments, the extraction tube 108 may extend into the downstream portion 92 such that an inlet to the extraction tube 108 is positioned lower than a bottom surface of the wall 96. The sampling port 100 may be closed by a sampling stop 158 that may selectively seal the sampling port 100. The inlet 104 to the fluid collection container 48 may be positioned above the inlet to the extraction tube 108.

It is noted that in FIGS. 4, 7, 8, 14, and 15 the dimensions are provided in millimeters. These dimensions are not meant to be limiting as one skilled in the art would appreciate adjustments in the size of the components shown.

Figure 10:
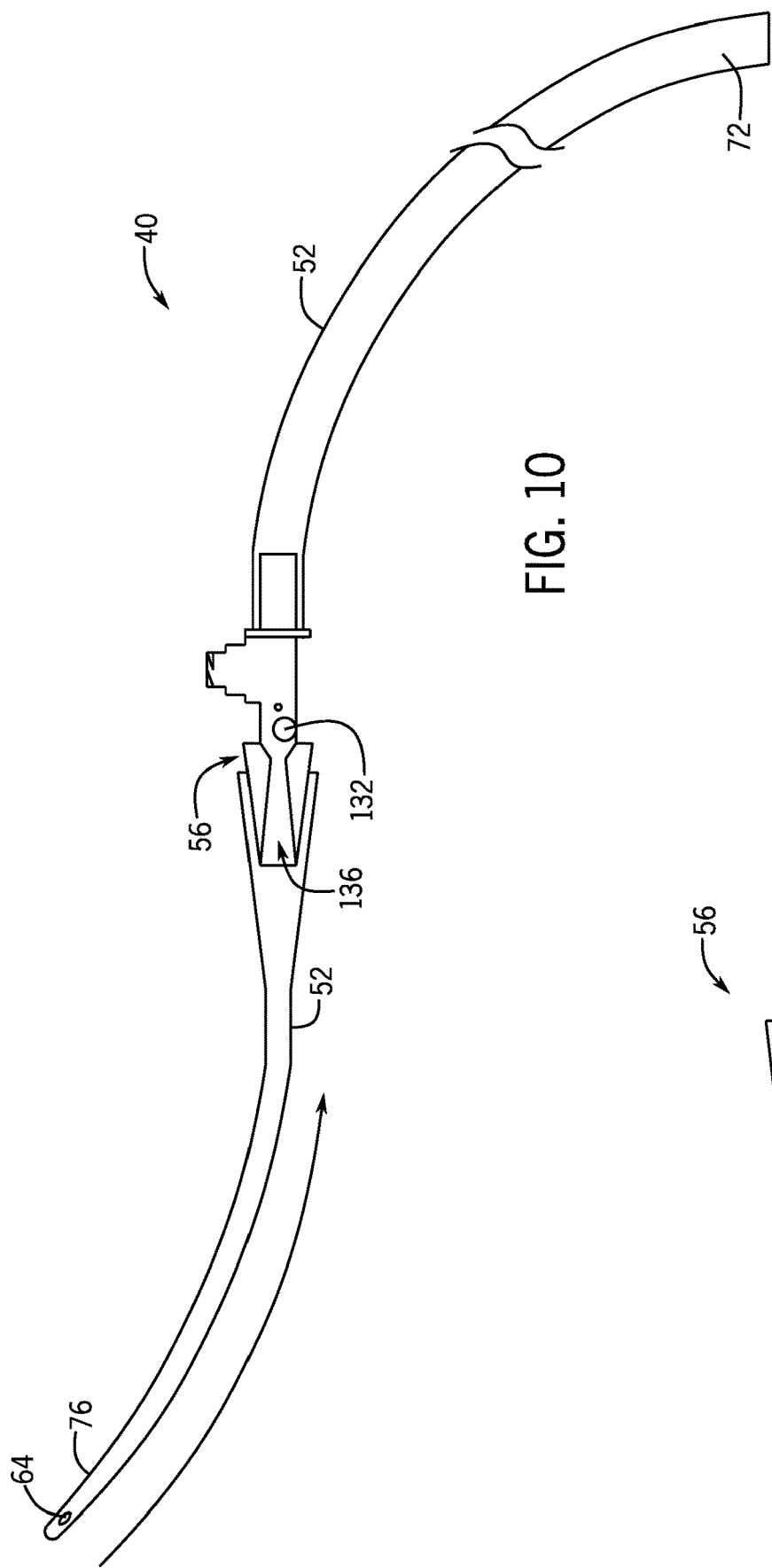
FIG. 10 is a partial side view of fluid tubing of the catheter system of FIG. 1.
Figure 11:
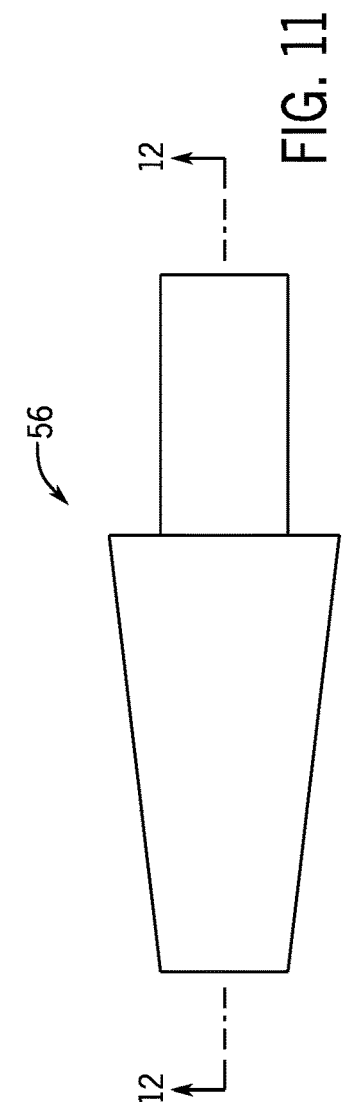
FIG. 11 is a top view of a check valve of the catheter system of FIG. 1.
Figure 12:
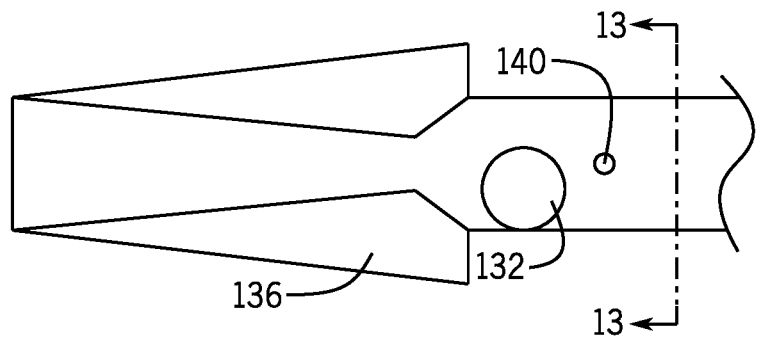
FIG. 12 is a cross-sectional view of the check valve of FIG. 11 taken along line-12-12 of FIG. 11.
Figure 13:
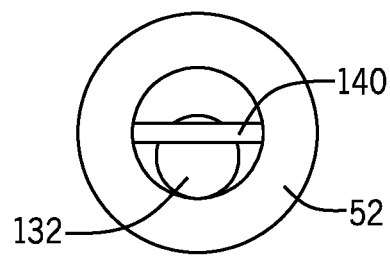
FIG. 13 is an end view of the check valve of FIG. 11 taken along line-13-13 of FIG. 12.
Figure 14:
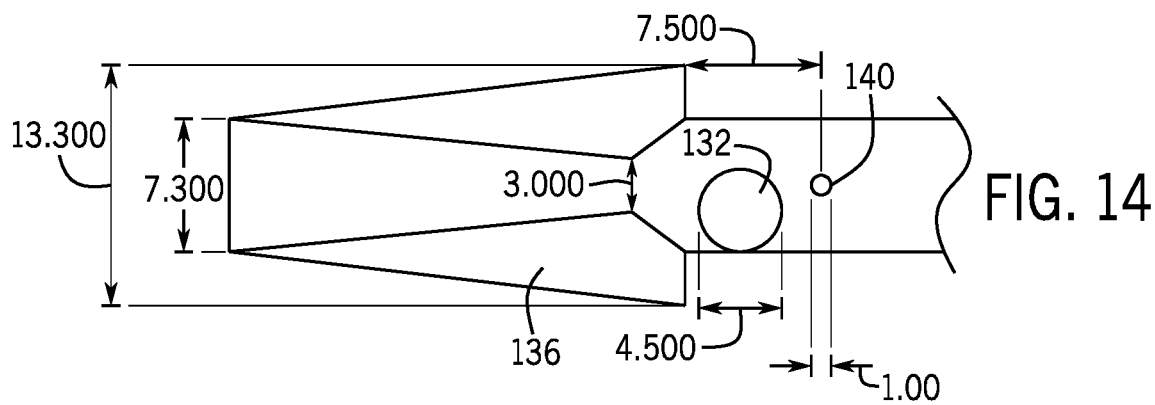
FIG. 14 is a dimensioned cross-sectional view, similar to FIG. 12, of the check valve of FIG. 11.
Figure 15:
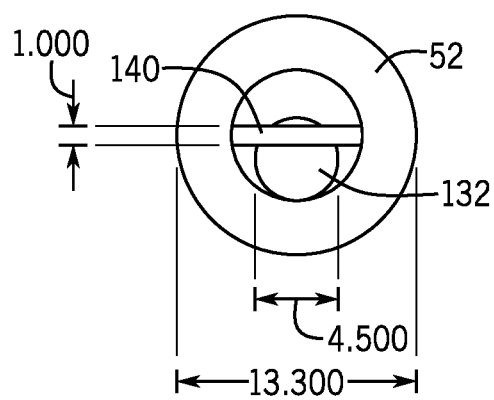
FIG. 15 is a dimensioned end view, similar to FIG. 13, of the check valve of FIG. 11.

FIG. 10 shows the catheter system 40 with the one-way check valve 56 disposed within the drainage lumen of the catheter tube 52 (i.e., along the intermediate portion of the catheter tube 52 between the proximal end 76 and the distal end 72). In some embodiments, the one-way check valve 56 may be a ball valve with a ball 132 and a valve seat 136. The ball 132 is positioned on the distal side of the valve seat 136. The ball 132 may have a diameter smaller than the diameter of the drainage lumen within the catheter tube 52.

FIGS. 11-15 show one embodiment of the check valve 56. The check valve 56 can include a valve body having the valve seat 136 with a tapered shape that provides a larger diameter at a proximal end that reduces to a minimum diameter that is smaller than the diameter of the ball 132, and expands at a distal end allowing the valve seat 136 to selectively receive the ball 132. The check valve 56 may also include a stop 140 that may be positioned distal to the ball 132 and, further, may be positioned in the catheter tube 52 at a height smaller than the height of the ball 132. The stop 140 extends across the diameter of the catheter tube 52 and may be cylindrical in shape. As such, the ball 132 may be positioned between the valve seat 136 and the stop 140.

Figure 16:
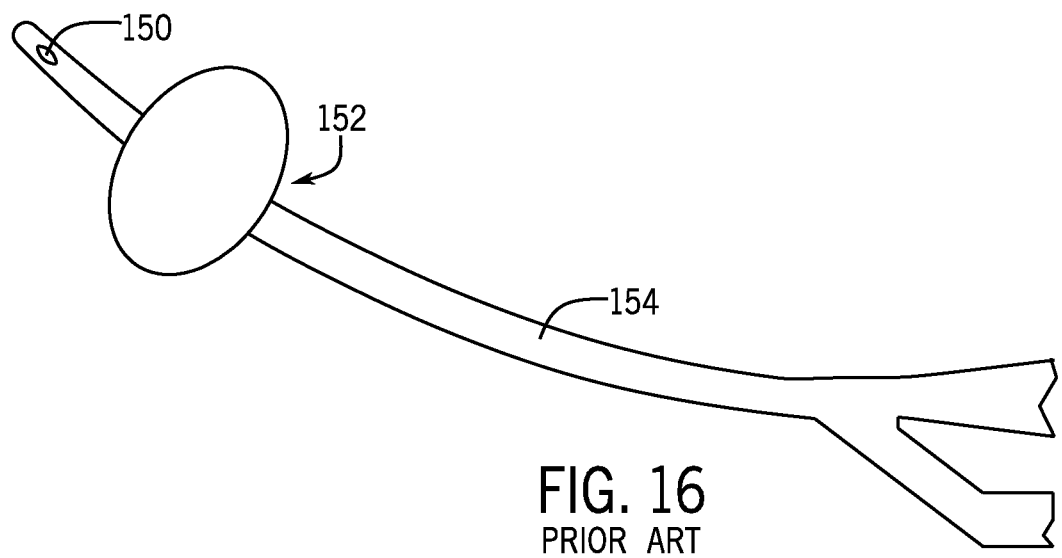
FIG. 16 is a side view of tubing and a balloon of a prior art urinary catheter.

FIG. 16 shows the tubing 154 and balloon 152 of a prior art urinary catheter with a singular opening 150 proximal to the balloon 152.

Figure 17:
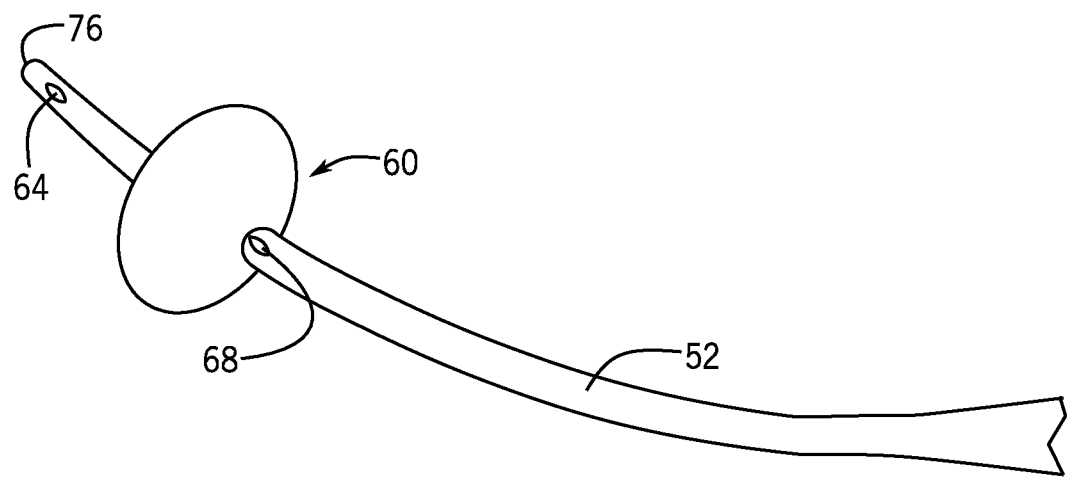
FIG. 17 is a side view of the tubing and balloon of the catheter system of FIG. 1.

FIG. 17 is a side view of the catheter tube 52 and balloon 60 of the catheter system 40 of FIG. 1. A balloon 60 may be positioned between the opening 64 and the second opening 68. The opening 64 may be proximal to the balloon 60 and the second opening 68 may be distal to the balloon 60. The opening 64 and the second opening 68 may provide fluid to enter the drainage lumen of the catheter tube 52. The balloon 60 may be arched and oval in shape. The balloon 60 may be connected to an inflation lumen (not shown) that is separate from the drainage lumen. The inflation lumen may provide fluid to the balloon 60 for inflation.

Now that the components of the catheter system 40 have been described in detail, the functionality of the catheter system 40 may be appreciated. The catheter system 40 is configured to drain fluid from a fluid source in the body. The proximal end 76 may be configured to be inserted into a subject and placed within a fluid source. The proximal end 76 including a portion of the catheter tube 52 appropriate for the size of the subject may remain in the subject during use. The balloon 60 may retain the proximal end 76 in a desired location in the subject during use. The balloon 60 may be configured to be inflated with a fluid via the inflation lumen when the proximal end 76 is in a desired location. In some embodiments, the desired location may be the bladder. In a non-limiting example, the balloon 60 may retain the proximal end 76 in the bladder by contacting interior walls of the bladder around the outlet at the base of the bladder. The opening 64 and the second opening 68 may communicate fluid from the bladder to the drainage lumen of the catheter system 40 when the subject's bladder contains fluid that reaches the level of the opening 64. When the bladder does not contain adequate fluid to reach the level of the opening 64, the second opening 68 may provide fluid communication to the drainage lumen. The second opening 68 may be positioned distal to the balloon 60 and the arched shape of the balloon 60 may allow fluid at the base of the bladder to communicate with the second opening 68 thereby draining the bladder of minimal amounts of residual fluid. Furthermore, if one of the opening 64 or the second opening 68 becomes clogged (e.g., has a clot that blocks the opening 64/68), the other opening 64/68 is still available for fluid drainage. In some embodiments, the fluid to be drained is urine. More specifically, in some embodiments, the balloon 60 is shaped with an arch and underneath the arch is the second opening 68. The second opening 68 may be directly at the urethra opening of a subject and therefore the bladder can remain empty and not house stagnant urine.

The fluid communicated from at least one of the opening 64 or the second opening 68 to the drainage lumen can travel through the drainage lumen within the catheter tube 52 to the one-way check valve 56. The one-way check valve 56 may be positioned outside of the subject when the proximal end 76 is positioned inside the subject (e.g., substantially or immediately adjacent to the body of the subject). The one-way check valve 56 may permit fluid communication traveling downstream from the proximal end 76 to the distal end 72. When fluid is communicating from the proximal end 76 to the distal end 72, the fluid presses the ball 132 off the valve seat 136 and against the stop 140, placing the one-way check valve 56 into the open position. If fluid begins to travel from the distal end 72 upstream toward the proximal end 76, the fluid will press the ball 132 against the valve seat 136, placing the one-way check valve 56 in the closed positon which blocks fluid flow from passing the one-way check valve 56. The stop 140 prevents the ball 132 from traveling outside of the one-way check valve 56 on the distal side and the valve seat 136 prevents the ball 132 from traveling outside of the one-way check valve 56 on the proximal side. Moreover, the regular movement of the ball 132 within the check valve 56 (e.g., via the regular flow of urine or other bodily fluids) provides benefits. For example, due to the regular movement of the ball 132, sediments (e.g., precipitated minerals from urine) would not be expected to accumulate within the check valve 56, which would potentially cause a partial or complete blockage of the catheter tube 52.

In some embodiments, the exterior of the one-way check valve 56 may be transparent. When the one-way check valve 56 is in the open position, fluid is allowed to flow through the drainage lumen in the catheter tube 52 to the distal end 72 of the catheter tube 52 and the fluid sampling component 44.

The fluid sampling component 44 receives fluid from the distal end 72 of the catheter tube 52 via the inlet 86 to the fluid sampling component 44. The inlet 86 permits fluid communication between the distal end 72 and the upstream portion 88 and the upstream portion 88 facilitates fluid communication to the downstream portion 92. The wall 96 forces fluid communication between the upstream portion 88 and the downstream portion 92 to occur below a bottom surface of the wall 96. In some embodiments, the fluid within the fluid sampling component 44 may be desirable for sampling. Fluid may be sampled from the fluid sampling component 44 using the sampling port 100 and the extraction tube 108. In a non-limiting example, a needle may be placed into the sampling port 100 and may extend through the extraction tube 108 into a bottom area of the downstream portion 92 of the fluid sampling component 44. Fluid not removed for sampling may travel around the extraction tube 108 and through the inlet 104 to the fluid collection container 48. The fluid collection container 48 is configured to receive an appropriate amount of fluid from the catheter system 40.

In some embodiments, the fluid sampling component 44 may facilitate the withdrawal of fluid for fluid testing or analyses. In a non-limiting example of urine drainage, and when a subject produces urine, the new urine entering the fluid sampling component 44 will push the old urine out and into the fluid collection container 48. This leads to fresh samples and reduces the likelihood of samples containing bacterial growth. In some embodiments, the fluid sampling component 44 may have an effective withdrawal volume of 17.8 milliliters (ml). One skilled in the art will appreciate that the fluid sampling component 44 can be any desired size larger or smaller than that shown and described.

Additional advantages to the design are apparent with respect to subject comfort. The location of the fluid sampling component 44 allows hospital staff to perform their tasks without disturbing the subject due to the fluid sampling component 44 being placed at the distal end 72 outside of the patient. In a non-limiting example, the fluid collection container 48 may be placed at a side of a patient bed or below a patient bed.

In some embodiments, the extraction tube 108 extends to the bottom of the fluid sampling component 44 while remaining 3 mm off of a bottom surface of the fluid sampling component 44. This ensures that the majority of the fluid can be extracted for testing. Before a syringe or needle is connected to the sampling port 100, urine cannot fill the straw as the sampling port 100 may be closed with the sampling stop 158, which can be any material such as plastic or rubber.

Thus, the invention provides an improved catheter system for draining urine from a bladder. The catheter system prevents urine backflow, improves bladder emptying, improves the prevention of system failure due to clotting, and improves the convenience of urine collection for culture. The catheter system reduces the potential for infection and improves turnaround time for urine collection. This improves efficiency and diagnosis, and reduces the likelihood of a hospital-acquired, catheter-associated urinary tract infection, which in return reduces length of stay and microbial resistance to the patient due to treatment.

Although the invention has been described in considerable detail with reference to certain embodiments, one skilled in the art will appreciate that the present invention may be practiced by other than the described embodiments, which have been presented for purposes of illustration and not of limitation. Therefore, the scope of the appended claims should not be limited to the description of the embodiments contained herein.

What is claimed is:

1. A catheter system configured for draining a bodily fluid from a fluid source in a body of a subject, the catheter system comprising:
   a catheter tube having a proximal end, a distal end, and an intermediate portion between the proximal end and the distal end, the catheter tube including a drainage lumen extending from a proximal end opening in the proximal end to a distal end opening in the distal end; and
   a one way check valve having an open position in which the bodily fluid can flow in a downstream direction from the proximal end toward the distal end, the check valve having a closed position in which the bodily fluid cannot flow in an upstream direction from the distal end toward the proximal end,
   the check valve being positioned in the drainage lumen at the intermediate portion of the catheter tube such that the check valve is configured to be outside of and adjacent to the body of the subject when the proximal end opening is located in the fluid source in the body of the subject, the check valve being a ball valve comprising a valve body having a valve seat, a stop, and a ball positioned between the valve seat and the stop, the ball sealing against the valve seat when the check valve is in the closed position, the stop restricting movement of the ball toward the distal end opening,
   wherein the stop extends across a diameter of the catheter tube at a height smaller than a height of the ball,
   wherein the valve seat extends through the valve body and has a tapered shape that, in the downstream direction, reduces in diameter to a minimum diameter and thereafter increases in diameter, the minimum diameter being smaller than the height of the ball;
   wherein the valve body includes a proximal opening, a distal opening, and a port located between the proximal opening and the distal opening and has a tapered external shape surrounding the valve seat that gradually increases in diameter in the downstream direction.

2. The catheter system of claim 1 wherein:
   the check valve is positioned at the intermediate portion adjacent to the proximal end.

3. The catheter system of claim 1 wherein:
   the catheter tube is comprised of at least two pieces that are connected together by the check valve.

4. The catheter system of claim 1 wherein:
   an exterior of the check valve is transparent.

5. The catheter system of claim 1, wherein the stop is cylindrical.

6. The catheter system of claim 1, wherein the stop extends across a center of the catheter tube.

7. The catheter system of claim 1 and further comprising a fluid sampling container in fluid communication with the distal end, the fluid sampling container having an upstream portion in fluid communication with the distal end and a downstream portion in fluid communication with the upstream portion.

8. The catheter system of claim 7, wherein the upstream portion is partially separated from the downstream portion by a wall.

9. The catheter system of claim 8 wherein the fluid sampling container includes a sampling port in fluid communication with the downstream portion.

10. The catheter system of claim 9, wherein the sampling port is in fluid communication with an extraction tube having an opening below the wall.

11. The catheter system of claim 7 wherein the downstream portion is in fluid communication with a fluid collection bag.

12. The catheter system of claim 7, wherein the fluid sampling container includes an inlet that interfaces with the distal end.

13. The catheter system of claim 1 and further comprising:
   a balloon positioned at the proximal end of the catheter tube,
   wherein the drainage lumen includes a second proximal end opening in the proximal end, and
   wherein the balloon is positioned between the opening at the proximal end of the catheter tube and the second proximal end opening in the proximal end of the catheter tube.

14. The catheter system of claim 13 wherein the catheter tube includes an inflation lumen in fluid communication with the balloon for inflating the balloon.

\* \* \* \* \*